United States Patent
Lambin et al.

(10) Patent No.: US 12,102,842 B2
(45) Date of Patent: Oct. 1, 2024

(54) TREATMENT AND PLANNING FOR LYMPHOCYTES SPARING RADIOTHERAPY

(71) Applicant: Universiteit Maastricht, Maastricht (NL)

(72) Inventors: Philippe Lambin, Bousval-Genappe (BE); Ludwig Jerome Dubois, Bilzen (BE)

(73) Assignee: Universiteit Maastricht, Maastricht (NL)

( * ) Notice: Subject to any disclaimer, the term of this patent is extended or adjusted under 35 U.S.C. 154(b) by 228 days.

(21) Appl. No.: 17/802,766

(22) PCT Filed: Feb. 26, 2021

(86) PCT No.: PCT/NL2021/050129
§ 371 (c)(1),
(2) Date: Aug. 26, 2022

(87) PCT Pub. No.: WO2021/172991
PCT Pub. Date: Sep. 2, 2021

(65) Prior Publication Data
US 2023/0094681 A1 Mar. 30, 2023

(30) Foreign Application Priority Data
Feb. 28, 2020 (NL) .................................. 2025017

(51) Int. Cl.
*A61N 5/10* (2006.01)
(52) U.S. Cl.
CPC ......... *A61N 5/1031* (2013.01); *A61N 5/1064* (2013.01); *A61N 5/1071* (2013.01); *A61N 2005/1087* (2013.01)
(58) Field of Classification Search
CPC .. A61N 5/1031; A61N 5/1064; A61N 5/1071; A61N 2005/1087; A61N 2005/1091
See application file for complete search history.

(56) References Cited

U.S. PATENT DOCUMENTS

| 2016/0339270 A1 | 11/2016 | Ellsworth et al. |
| 2019/0022411 A1 | 1/2019 | Parry et al. |
| 2019/0070435 A1 | 3/2019 | Joe Anto et al. |

FOREIGN PATENT DOCUMENTS

| KR | 101882300 B1 | 7/2018 |

OTHER PUBLICATIONS

Ellsworth et al., "Comprehensive Analysis of the Kinetics of RadiationInduced Lymphocyte Loss in Patients Treated with External Beam Radiation Therapy", Radiation Research, vol. 193, pp. 73-81. (Year: 2020).*

(Continued)

*Primary Examiner* — Kiho Kim
(74) *Attorney, Agent, or Firm* — Banner & Witcoff, Ltd.

(57) ABSTRACT

The present document relates to providing a radiation treatment plan for treatment of a neoplasm, including the steps of: obtaining an image including the neoplasm and obtaining first segmentation data for segmenting at least one target-volume to be targeted with radiation. Further identifying any organs-at-risk and segmenting these. The method further comprises identifying lymphocyte-rich-organs in the image, and obtaining third segmentation data for segmenting the lymphocyte-rich-organs. The planning system then obtains radiation dose regime data, including first, second and third dose regime data. The planning system then determines a radiation treatment plan which provides treatment process parameters for operating one or more radiation beams for radiation treatment of the neoplasm, The process parameters are determined to apply the radiation at a first radiation dose to the target volume which corresponds with the first dose regime data, apply the radiation at a minimized second radiation dose to the or each organs-at-risk, and apply the radiation at a third radiation dose to the or each lymphocyte- (Continued)

rich-organ which corresponds with the third dose regime data, wherein the third radiation dose amount is minimized.

34 Claims, 7 Drawing Sheets

(56) References Cited

OTHER PUBLICATIONS

International Search Report and Written Opinion—PCT/NL2021/050129—mailing date Sep. 2, 2021.

* cited by examiner

TREATMENT AND PLANNING FOR LYMPHOCYTES SPARING RADIOTHERAPY

CROSS-REFERENCE TO RELATED APPLICATIONS

This application is a U.S. National Stage application under 35 U.S.C. § 371 of International Application PCT/NL2021/050129 (published as WO 2021/172991 A1), filed Feb. 26, 2021 which claims the benefit of priority to Application NL 2025017, filed Feb. 28, 2020. Benefit of the filing date of these prior applications is hereby claimed. Each of these prior applications is hereby incorporated by reference in its entirety.

FIELD OF THE INVENTION

The present invention relates to improvements in the field of radiation treatment performed for treatment of a neoplasm. The invention amongst others is directed at a method of providing a radiation treatment plan for treatment of a neoplasm in a human or animal body using a planning system, the method including the steps of: obtaining, by the planning system using at least one imaging system, an image of at least a part of the body including the neoplasm; obtaining, by the planning system, first segmentation data for segmenting, in the image, at least one target volume to be targeted with radiation; identifying, by the planning system, one or more organs-at-risk in the image, and obtaining second segmentation data for segmenting the or each organs-at-risk. Furthermore, the invention is directed at a treatment method and a radiation treatment planning system.

A tumor is considered clinically treatment resistant when it insufficiently responds to treatment by radiotherapy alone or in combination with chemotherapy, immunotherapy, hormonotherapy, targeted agents, surgery or any other treatment. One of the major known causes of radio resistance and resistance to systemic therapy (e.g. chemotherapy, targeted agents, hormonal therapy as well as immunotherapy), is inefficiency of the immune system mediated by the "good" immune cells the CD8+ lymphocytes, the NK cells, the neutrophils, the dendritic cells and the macrophage type 1. Therefore it has been show that hematological toxicity in particular late lymphopenia has a strong negative prognostic value across different cancer type. Thus, a decreased number of immune cells, induced by the treatment in particular lymphocytes makes it more radio resistant and/or resistant to systemic therapy. Furthermore, hematological toxicity in particular lymphopenia increase the risk of infections.

SUMMARY

It is intended to decrease the risk of treatment-induced lymphopenia and expected increased probability of unsuccessfully treating a patient with radiotherapy (alone or in combination with another treatment) and to decrease the risk of infections.

To this end, there is provided herewith a method of providing a radiation treatment plan for treatment of a neoplasm in a human or animal body using a planning system, the method including the steps of: obtaining, by the planning system using at least one imaging system, an image of at least a part of the body including the neoplasm; obtaining, by the planning system, first segmentation data for segmenting, in the image, at least one target volume to be targeted with radiation; identifying, by the planning system, one or more organs-at-risk in the image, and obtaining second segmentation data for segmenting the or each organs-at-risk; wherein the method further comprises: identifying, by the planning system and in addition to the identified organs-at-risk, one or more lymphocyte-rich-organs in the image, and obtaining third segmentation data for segmenting the or each lymphocyte-rich-organ; obtaining, by the planning system, radiation dose regime data, wherein the radiation dose regime data includes a first dose regime data for the target volume, second dose regime data for the or each organ-at-risk, and third dose regime data for the or each lymphocyte-rich-organ, wherein the second dose regime data is different form the first dose regime data and wherein the third dose regime data is different from the second dose regime data and different from the first dose regime data; determining, by the planning system, a radiation treatment plan, wherein the radiation treatment plan provides treatment process parameters for operating one or more radiation beams for radiation treatment of the neoplasm, wherein the process parameters provided by the radiation treatment plan are determined such as to: apply the radiation at a first radiation dose to the target volume which corresponds with the first dose regime data; apply the radiation at a minimized second radiation dose to the or each organs-at-risk which corresponds with the second dose regime data; and apply the radiation at a third radiation dose to the or each lymphocyte-rich-organ which corresponds with the third dose regime data, wherein the third radiation dose amount is minimized.

To achieve lymphocytes sparing radiotherapy, the above method in accordance with the invention, in addition to focusing the treatment planning on avoiding as much as possible radiation damage to organs-at-risk (OAR's), also identifies a second class of body structures and organs to be handled with care. These are the body structures (e.g. organs) that are rich of lymphocytes and lymphocyte bearing tissue. One part of these are the structures rich in blood (SRB) such as those taking part in blood circulation, for example the heart, vessels, lungs and liver. Another part of these are the structures rich in (precursors of) non-circulating lymphocytes (SRL), which for example include non-invaded lymph nodes, the spleen, bone-marrow and optionally the thymus. It is to be noted that that one differentiate the a) the organs or structure rich in circulating lymphocytes or rich in blood that also sensitive to the dose rate (DR) of irradiation and Beam-On-Time (DOT), which is associated with beam energy and dose rate and b) the organs or structure rich in non-circulating lymphocytes or its precursor such as the nodes, the spleen and the bone marrow that are less or not sensitive to DIR or BOT).

For these latter class of body structures. i.e. the body structures (e.g. organs) that are rich of lymphocytes and lymphocyte bearing tissue, generally herein referred to as the lymphocyte-rich-organs (LRO's), the method introduces an additional radiation dose regime, herein referred to as the third radiation dose regime, that distinguishes from the dose regime applied to the conventionally considered organs-at-risk (i.e. the second radiation dose regime). It is to be noted that some of the conventional organs-at-risk may also be rich of lymphocytes, such as the heart or lungs, and thus also belong to the class of lymphocyte-rich-organs. For these organs (in the present document sometimes referred to as lymphocyte-related organs at risk (LOAR's)), as may be appreciated, both the second and the third radiation dose regime applies.

Advantageously, in order to decrease the risk of treatment-induced lymphopenia and expected probability of unsuccessfully treating of a patient with radiotherapy, systemic therapy or other treatment, the present invention enables to provide a treatment plan that systematically spares the blood and the organs rich in lymphocytes. This is achieved by a) segmenting the lymphocyte-rich-organs (LRO), i.e. the body structures that are rich in lymphocytes, b) planning a treatment in a treatment planning system that spares the segmented lymphocyte-rich-organs while maintaining the first radiation dose regime for irradiation of the target volume including the tumor (the gross tumor volumes, the clinical target volume, the planning target volume), and c) to implement the radiation treatment plan by performing such irradiation accordingly. The invention thereby provides a affordable method of planning the treatment and/or treating with radiation a neoplasm with lymphocytes sparing radiotherapy in a human or animal body. The inventive approach is comparable to a new immunotherapeutic drug at the difference that it use a smart, not yet used and optionally AI-based method to plan or give radiation. This method allow to decrease treatment-induced lymphopenia, improve the intrinsic or treatment induced immune effect, decrease the risk of infections and therefore improve the outcome of the treatment at moderate costs.

Typically, the second radiation dose regime is directed at minimizing the radiation dose to the OAR's while achieving the first radiation dose according to the first radiation dose regime to the target volume (e.g. the GTV, CTV and/or PTV, see below). The third dose regime primarily is directed at protecting as much as possible, i.e. while achieving the first radiation dose according to the first radiation dose regime, the damage to lymphocytes. In the first place, this can be achieved by keeping the dose received by the radiation affected lymphocytes as low as possible (and limit the percentage of lymphocytes irradiated above the threshold of lymphocyte mortality).

Another issue, however, is that blood is a moving organ and therefore spatial sparing of the LRO's with advanced planning and/or particle therapies is not always possible and not always enough. Therefore to complement the protective effect of dose constraints, e.g. in cases the tumor is so large that it is not possible to protect the lymphocytes sufficiently, this may be achieved by applying the required dose in an as short as possible time duration and/or in an as small as possible volume of the LRO's in order to spare as many lymphocytes as possible. In this respect, it is to be realized that lymphocytes are mobile (i.e. with the blood bearing them) and that increasing the dose rate for example enables to apply the same dose in a less time. Therefore, less lymphocytes travel and recirculate through the irradiated area of the LRO's if the duration of the radiation treatment can be shortened. Thus, if the original provided treatment plan obtained is insufficient or satisfactory but not optimal, the irradiation time or the dose rate provide important further process parameters to obtain additional protection of the lymphocytes. For a given irradiated volume a higher dose rate of the irradiation or a shorter irradiation time, e.g. with a more radioactive source, an irradiation closer to the target, a flattening Free filter (FFF) irradiation, a radiation with higher energy or FLASH irradiation, will be beneficial because this has a lower impact on the number of lymphocytes killed by radiation. Therefore, in accordance with some embodiments, for enabling to apply a third radiation dose to the or each lymphocyte-rich-organ which corresponds with the third dose regime data, the step of determining a radiation treatment plan further includes determining the process parameters such as to apply the third radiation dose with a maximized dose rate for decreasing an irradiation time duration. The increase of the dose rate or the shortening of the irradiation time duration may, optionally, be applied together with releasing the original absolute dose restriction of the third radiation dose regime, in particular for the SRB containing circulating cells, less so for the SRI, containing non-circulating cells, as a trade-off to obtain an even higher dose in the target volume in cases wherein this may be desired.

In some of examples of these embodiments, for decreasing the irradiated volume, the process parameters are determined such as to include, when clinically validated, at least one of: to avoid elective nodal irradiation (ENI), which is the delivery of a radiation dose to the uninvolved regional lymph node area at risk for microscopic disease, but rather to favor involved field radiotherapy (IFRT); to segment the involved nodes based on imaging or biopsy or fine needle aspiration and irradiate those involve nodes as target volume rather than to irradiate the totality of the nodes levels.

In some of examples of these embodiments, for maximizing the dose rate or decreasing the beam-on-time the process parameters are determined such as to include at least one of: an indication of a type of radiation source to be applied, wherein the indicated type of radiation source is determined for maximizing a radiation source activity, such as a Cobalt 60 or Iridium 192 radiation source. Using a more active source for external beam of brachytherapy directly increases the applied dose rate. In another embodiment for maximizing the dose rate, the process parameters are determined such as to include an indication of a distance between a radiation source and a target volume or a patient such as to achieve the maximized dose rate. Here the distance may be reduced until a distance is obtained wherein a given dose rate is obtained. This may be done with or without applying a more active radiation source. Furthermore, another process parameter that may be used to obtain higher dose rates may include an indication to apply a radiation source in absence of a flattening filter (Flattening filter free or FFF) to get >2000 Monitor Units (MU) per minutes. Furthermore, another process parameter that may be used to obtain higher dose rates may include an indication to optimize beam energy to decrease beam-on-time. Furthermore, another process parameter that may be used to obtain higher dose rates and lower Beam-On-Time may include an indication to apply an optimized energy e.g. 10 MV rather than 6 MV for a deep lesion. Furthermore, for maximizing the dose rate the process parameters are determined such as to include an indication to perform a FLASH irradiation. Here the FLASH irradiation, for example with electrons or protons or photons, may include irradiating with a dose rate of at least 40 Gray per second, preferably at least 50 Gray per second, for a duration of at most 500 milliseconds preferably less than 200 milliseconds, dose rate within the pulse higher then 1.8 $10^5$ Gy/sec, using a radiation type selected from a group comprising: electrons, protons, photons, ions such as carbon ions, photons, or particles.

In some embodiments, the method includes, for enabling to apply a third radiation dose to the or each lymphocyte-rich-organ which corresponds with the third dose regime data, the step of determining a radiation treatment plan further includes determining the process parameters such as to include an indication of a radiation type providing a sufficient Bragg peak such as proton or carbon ion radiation, and an indication of an intended location of the Bragg peak such as to focus the Bragg peak in the target volume. For example, using proton radiation a strong Bragg peak may be obtained, which may be focused in the patient's body by modifying the beam or field parameters (e.g. intensity, energy, use of filters) such that the Bragg peak primarily hits the target volume and as little as possible LRO's.

In some embodiments, the method includes, for enabling to apply a third radiation dose to the or each lymphocyte-rich-organ which corresponds with the third dose regime data, the step of determining a radiation treatment plan further includes determining the process parameters such as to at least one of: apply the radiation at the first radiation dose at the target volume with a minimal number of radiation beams; or apply the radiation at the first radiation dose at the target volume using a maximized number of non-moving beams, preferably using only static beams. This strategy is directed at reducing the "low dose bath" (lymphocytes being killed by low radiation dose) and the radiation affected area as much as possible. The more beams or fields, the larger the radiation affected area. Also, moving beams (such as rotating beams) spread the radiation over a larger area of the body. Thus to reduce the radiation affected area, and hence the amount of lymphocytes that receive radiation, reducing the number of beams and/or number of moving beams is advantageous.

In some embodiments, the method includes providing the process parameters in the radiation treatment plan such as to apply an adaptive radiation treatment plan, wherein the neoplasm is irradiated during a number of fractions over a period of time, more fractions killing more lymphocytes, and wherein the process parameters are adapted to, whenever validated clinically as isoeffective and isotoxic, to hypofractionate the radiation treatment, to decrease the number of fraction and increase the dose per fraction in view to have the same effect on the tumour, the same toxicity but a decreased killing effect on the lymphocytes.

In some embodiments, the method includes providing the process parameters in the radiation treatment plan such as to apply an adaptive radiation treatment plan, wherein the neoplasm is irradiated during a number of fractions over a period of time, and wherein the process parameters are adapted for each fraction for minimizing the third radiation dose during the respective fraction. As the tumour volume, the blood flow and the size of irradiated organs, the OAR or the LRO, may change during treatment, updating the treatment plan, based on, for example, online or offline imaging such as kV. MV imaging, echography, Magnetic Resonance with or without a MR linac, any imaging of the blood volume or blood flow (such as the venography technique or velocity-selective (VS) pulse trains), any imaging of (sub-type of) lymphocytes or neutrophils, prior to each fraction enables to even further reduce the number of radiation affected lymphocytes.

In some embodiments, the third dose regime data indicates that each lymphocytes-rich-organs has high-optimal or moderate or minimum dose constraints that can be expressed as the applied Mean Dose (MD) lower than a threshold or as Dose Volume histogram (percentage or volume in cubic centimeters (cc) or milliliters (ml) of an organ receiving a dose lower than a certain threshold dose). An example of dose constraints would be the following Mean Dose (MD) per structure (SRB)

Optimal: <8% of the prescribed dose (e.g. ≤5 Gy to the heart for a prescribed dose of 60 Gy in 30 fractions ($MD_{Heart}$=≤5 Cy)

Moderate: <18% of the prescribed dose (e.g. ≤11 Gy to the heart for a prescribed dose of 60 Cy in 30 fractions ($MD_{Heart}$=≤11 Gy)

Minimum: <33% of the prescribed dose (e.g. ≤20 Gy to the heart for a prescribed dose of 60 Gy in 30 fractions ($MD_{Heart}$=≤20 Gy)

An example of dose volume constraints for the pelvic bone marrow (BM), it would be a low volume receiving ≥40 Gy ($V_{Lung\text{-}40\ Gy}$<100 cc) or for lung a $V_{Lung\text{-}5\ Gy}$: <50%.

Furthermore in some embodiments, the lymphocyte-rich-organs include one or more of a group comprising: a heart; a large blood vessel, such as a thoracic aorta, an abdominal aorta, the superior or inferior vena cava, a carotid or any large artery (the iliac, mesenteric, subclavian, femoral arteries . . . ); a heart ventricle or atrium, such as any one or more of the left and right ventricle and the left and right atrium; a spleen; a bone; a bone marrow; a brain; a lung, the thymus.

In the above, in some embodiments, the process parameters may include (but are not limited to) one or more of a group comprising: a mean dose per organ indication, such as an absolute dose or a relative dose of the prescribed dose (according to the ICRU recommendations), a dose per volume, or a dose per weight; a dose rate indication, such as an absolute dose rate, a dose rate per volume, monitor units per minutes or a dose rate per weight; a number of fraction, dose per fraction, the proportion of inactivated circulating/non-circulating or total lymphocytes, radiation doses to circulating cells, a number of radiation sources to be applied; a type of radiation source to be applied; a distance between a radiation source and a target volume or a patient; indications of a filter to be used with one or more radiation sources; an indication of radiation intensity to be applied over time, such as a FLASH radiation profile (mean dose rate, dose per pulse, number of pulse, dose rate within the pulse (Gy/s)), dose rate within the pulse (Gy/s) and overall time of irradiation); irradiation time duration: an indication on whether or not to apply a flattening filter; an indication on beam focusing; an indication on an intended location of a Bragg peak and its range uncertainty and indication on further treatment steps, such as a necessity of a blood or (a selection of a subclass of and/or engineered and/or expanded an/or autologous and/or allogenic) lymphocytes transfusion or treatment with a lymphocyte growth factor after irradiation.

In accordance with a second aspect of the invention, there is provide a radiation treatment planning system configured for determining a treatment plan for treatment of a neoplasm in a human or animal body, the system including or being communicatively connectable to a data storage element for storing data, and comprising a controller, wherein the controller is configured for receiving instructions and for enabling the system to perform the steps of: obtaining, by the planning system using at least one imaging system, an image of at least a part of the body including the neoplasm; obtaining, by the planning system, first segmentation data for segmenting, in the image, at least one target volume to be targeted with radiation; identifying, by the planning system, one or more organs-at-risk in the image, and obtaining second segmentation data for segmenting the or each organs-at-risk; wherein the method further comprises: identifying, by the planning system and in addition to the identified organs-at-risk, one or more lymphocyte-rich-organs in the image, and obtaining third segmentation data for segmenting the or each lymphocyte-rich-organ; obtaining, by the planning system, radiation dose regime data, wherein the radiation dose regime data includes a first dose regime data for the target volume, second dose regime data for the or each organ-at-risk, and third dose regime data for the or each lymphocyte-rich-organ, wherein the second dose regime data is different form the first dose regime data and wherein the third dose regime data is different from the second dose regime data and different from the first dose regime data; determining, by the planning system, a radiation treatment plan, wherein the radiation treatment plan provides treatment process parameters for operating one or more radiation beams for radiation treatment of the neoplasm, wherein the process parameters provided by the radiation treatment plan are determined such as to: apply the radiation at a first radiation dose to the target volume which corresponds with the first dose regime data; apply the radiation at a minimized second radiation dose to the or each organs-at-risk which corresponds with the second dose regime data; and apply the radiation at a third radiation dose to the or each lymphocyte-rich-organ which corresponds with the third dose regime data, wherein the third radiation dose amount is minimized.

In accordance with a third aspect, there is provided a method of treating a patient with radiation treatment, where the patient is suffering from neoplasm growth, wherein the radiation treatment is performed in accordance with a radiation treatment plan for treatment of a neoplasm in the patient's body, the method including the steps of: obtaining, using at least one imaging system, an image of at least a part of the body, wherein the part of the body includes the neoplasm; segmenting in the image at least one target volume to be targeted with radiation; identifying one or more organs-at-risk in the image and segmenting the or each organ-at-risk; wherein the method further comprises: identifying, in addition to the identified organs-at-risk, one or more lymphocyte-rich-organs in the image, and segmenting the or each lymphocyte-rich-organ; determining a radiation dose regime, wherein the radiation dose regime includes a first dose regime for the target volume, a second dose regime for the or each organ-at-risk, and a third dose regime for the or each lymphocyte-rich-organ, and wherein the first dose regime, the second dose regime and the third dose regime are different from each other; determining the radiation treatment plan by determining treatment process parameters for operating one or more radiation beams for said radiation treatment of the neoplasm, wherein the process parameters are determined such as to: apply the radiation at a first radiation dose to the target volume which corresponds with the first dose regime; apply the radiation at a minimized second radiation dose, which corresponds with the second dose regime, to the or each organ-at-risk; and apply the radiation at a third radiation dose, which corresponds with the third dose regime, to the or each lymphocyte-rich-organ, wherein the third radiation dose amount is minimized.

In some embodiments, the process parameters include one or more of a group comprising: a mean dose per organ indication, such as an absolute dose or a relative dose of the prescribed dose (according to the ICRU recommendations), a dose per volume, or a dose per weight; a dose rate indication, such as an absolute dose rate, a dose rate per volume, monitor units per minutes or a dose rate per weight; a number of fraction, dose per fraction, the proportion of inactivated circulating/non-circulating or total lymphocytes, radiation doses to circulating cells, a number of radiation sources to be applied; a type of radiation source to be applied; a distance between a radiation source and a target volume or a patient; indications of a filter to be used with one or more radiation sources; an indication of radiation intensity to be applied over time, such as a FLASH radiation profile (mean dose rate, dose per pulse, number of pulse, dose rate within the pulse (Gy/s); irradiation time duration: an indication on whether or not to apply a flattening filter; an indication on beam focusing; an indication on an intended location of a Bragg peak; an indication on further treatment steps, such as a necessity of a blood transfusion or treatment with a lymphocyte growth factor after irradiation.

In some embodiments, the step of determining a treatment plan includes a step of: determining a preliminary treatment plan and calculating a third radiation dose that will be received by the or each lymphocyte-rich-organ what radiation treatment is performed in accordance with the preliminary radiation treatment plan; comparing the calculated third radiation dose with a dose threshold for the or each lymphocyte-rich-organ, and in case the calculated third radiation dose exceeds the optimal dose threshold, perform one or more modified treatment steps in accordance with a modified treatment plan different from the preliminary treatment plan. The benefits have been explained above to reduce the number of affected lymphocytes overall, even though the affected lymphocytes may not be optimally spared.

In some embodiments, the one or more modified treatment steps include applying the third radiation dose with a maximized dose rate for decreasing an irradiation time duration. For example in some embodiments, for applying the third radiation dose with the maximized dose rate, the method includes one or more of the following steps: applying the radiation using a type of radiation source with a radiation source activity of at least 20 terabecquerel per gram (TBq/g, such as a Cobalt 60 radiation source; applying the radiation at a distance between a radiation source and a target volume or a patient determined such as to achieve the maximized dose rate; applying the radiation using a radiation source in absence of a flattening filter; applying the radiation by performing a FLASH irradiation method, wherein the FLASH irradiation method includes irradiating with a dose rate of at least 40 Gray per second, preferably at least 50 Gray per second, for a duration of at most 500 milliseconds, preferably at most 200 milliseconds, using a radiation type selected from a group comprising: electrons, protons, ions such as carbon ions, photons, or particles. The one or more modified treatment steps may in accordance with some embodiments further include applying the radiation using a radiation type providing a Bragg peak, such as proton radiation, and modifying the radiation beam such as to focus the Bragg peak in the target volume. Furthermore, the modified treatment steps may include any of applying the radiation using at the first radiation dose at the target volume with a minimal number of radiation beams; or applying the radiation at the first radiation dose at the target volume using a maximized number of non-moving beams, preferably using only static beams.

In some cases, e.g. if the above mentioned approaches are not possible, not feasible, or still do not achieve the desired results, there are still two options for modifying the treatment of the patient. For example, some blood may be taken prior to radiation treatment which may be reinjected after the treatment. This will inject healthy lymphocytes back into the patient's body. One can also reinject lymphocytes that are engineered to produce specific chimeric antigen receptors (CARs) on their surface in the context of CAR-T cell therapy and expanded in vitro before reinjection. The same procedure of injection of (selection of subtypes of lymphocytes and/or engineered and/or expanded lymphocytes) can be done with allogenic or synthetic lymphocytes rather than autologous lymphocytes. Furthermore, additionally or alternatively, the patient may be treated with a specific lymphocytes growth factor in order to stimulate lymphocyte growth such as Interleukine-7. In case of a concomitant chemo-radiotherapy, one can decide to administer a chemotherapy that has less hematological toxicity for example lower dose or gemcitabine in place of cis-platin).

In some embodiments, the method includes applying an adaptive radiation treatment plan, wherein the neoplasm is irradiated during a number of fractions over a period of time, more fractions killing more lymphocytes, and wherein the process parameters are adapted to, whenever validated clinically as isoeffective and isotoxic, to hypofractionate the radiation treatment, to decrease the number of fraction and increase the dose per fraction in view to have the same effect on the tumour, the same toxicity but a decreased killing effect on the lymphocytes.

In some embodiments, the method includes applying an adaptive radiation treatment plan, wherein the neoplasm is irradiated during a number of fractions over a period of time, and wherein the process parameters are adapted for each fraction for minimizing the third radiation dose during the respective fraction. As the tumour volume, the blood flow and the size of irradiated organs, the OAR or the LRO, may change during treatment, updating the treatment plan, based on, for example, online or offline imaging such as kV, MV imaging, echography, Magnetic Resonance with or without a MR linac, any imaging of the blood flow, any imaging of (subtype of) lymphocytes, prior to each fraction enables to even further reduce the number of radiation affected lymphocytes.

In some embodiments, the image obtained for planning is a three dimensional image. Furthermore, the at least one imaging system may be configured for applying multiple image modalities, or images may be obtained from multiple imaging systems applying a various modalities.

The lymphocyte-rich-organs include one or more of a group comprising: a heart; a large blood vessel, such as a thoracic aorta, an abdominal aorta, the superior or inferior vena cava, a carotid or any large artery (the iliac, mesenteric, subclavian, femoral arteries . . . ); a heart ventricle or atrium, such as any one or more of the left and right ventricle and the left and right atrium; a spleen; a bone; a bone marrow; a brain; a lung, the thymus.

BRIEF DESCRIPTION OF THE DRAWINGS

The invention will further be elucidated by description of some specific embodiments thereof, making reference to the attached drawings. The detailed description provides examples of possible implementations of the invention, but is not to be regarded as describing the only embodiments falling under the scope. The scope of the invention is defined in the claims, and the description is to be regarded as illustrative without being restrictive on the invention. In the drawings:

DETAILED DESCRIPTION

Figure 1:
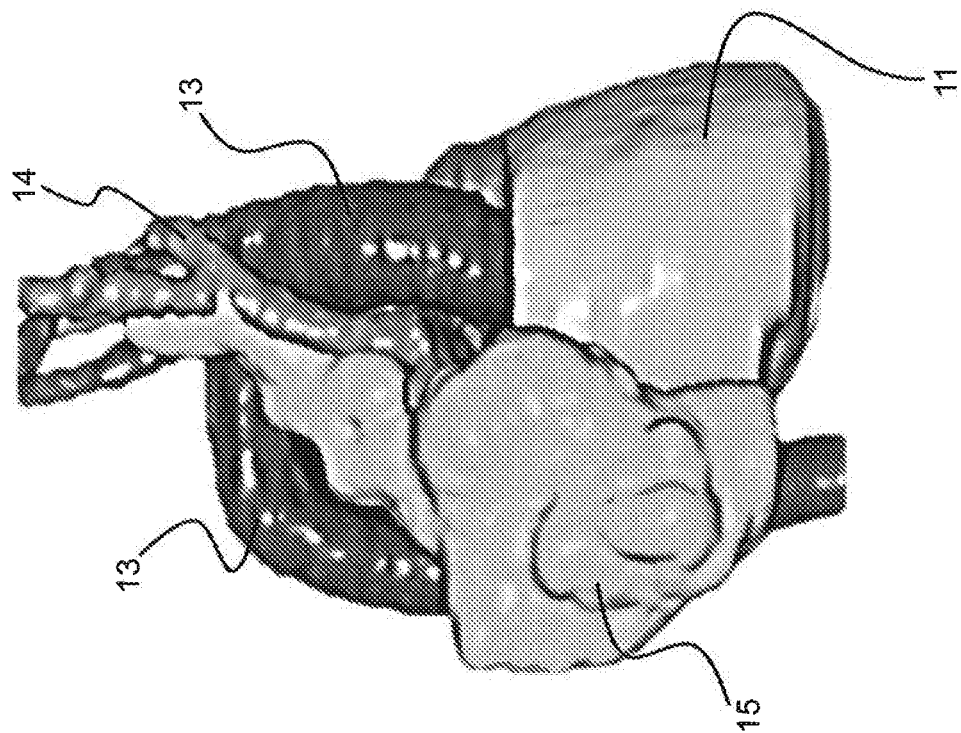
FIG. 1 provides an example of a segmentation for lung cancer treatment, during a method of the invention.
Figure 1:
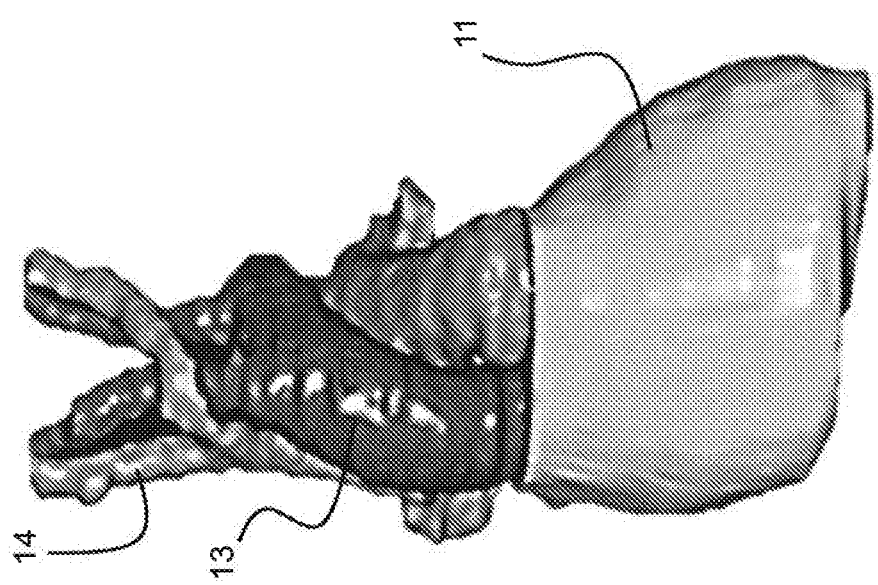

There is now strong clinical and preclinical evidence that lymphocytes, e.g. CD8+ T cells, are key effectors of immunotherapy and that irradiation of structure with circulating blood (large blood vessels, the heart) and lymphoid organs (including nodes, spleen, bones containing bone marrow, and thymus in children and young adults) causes transient or persistent lymphopenia. Furthermore, there is extensive clinical evidence, across multiple cancer sites and treatment modalities, that lymphopenia correlates strongly with decreased overall survival, tumour relapse and increased risk of infections. At the moment, the effect of radiation on lymphocytes is not taken into account in routine care. The present invention intends to improve the efficacy of radiotherapy and provide strategies to predict and prevent treatment-related lymphopenia. We recommend the application of the principle of As Low As Reasonably Achievable (ALARA) to lymphocyte rich regions for radiotherapy treatment planning to reduce the radiation doses to these structures, thus moving toward "Lymphocyte-Sparing Radiotherapy".

The Pacific trial, a randomised phase 3 trial in non-metastatic, advanced NSCLC, represented a breakthrough in immuno-oncology treatment (IO) within radiation oncology, convincingly demonstrating that adjuvant IO, after normofractionated standard chemoradiotherapy, can improve progression-free survival (PFS). Remarkably, the radiotherapy (RT) schedules of the Pacific trial were neither standardised nor optimised, as these were based only on investigator or radiation oncologist choice for each individual patient (total dose 54 Gy-74 Gy). Separately, it has been shown that RT is a double-edged sword regarding immune effects: it has both an immunostimulatory effect but also an immunosuppressive effect. IO might reduce or overrule this RT-related immunosuppression. Furthermore, lower doses to the heart, circulating blood pool, and lymphoid organs are associated with reduced immunosuppressive effect. It can thus be hypothesised that an optimised RT protocol has the potential to decrease the immunosuppressive effects of RT, e.g. by reducing RT-related lymphopenia (LP).

Several studies have shown that low blood lymphocyte count at baseline, across a range of cancer types, is a negative predictor of outcome. Furthermore, the presence of CD8$^+$ tumour infiltrating lymphocytes (TILs) on pathology review is a well-established predictor of better overall survival. Additionally, preclinical experiments with lymphocyte depletion, i.e. decreased CD4$^+$ and CD8$^+$ counts, have clearly established a causal relationship with reduced efficacy of radiotherapy and (radio)-IO.

The effect of RT on LP is well-documented and has been extensively described for several decades. Typically, LP is a transient phenomenon with a recovery within three months after RT, but in certain cases it can continue to persist even years after treatment which has been correlated to RT dose, RT sites, (hyper)fractionation, adjuvant chemotherapy, and irradiated volume. A causal relationship between RT-induced LP and adverse loco-regional control or survival has been speculated but not confirmed.

I. The Radiobiology of Lymphocytes

Lymphocytes are located in the blood (circulating lymphocytes), in reservoir lymphoid organs such as the spleen, and the thymus (in children and teenagers), in lymph nodes, and in the bone marrow, which is continuously producing new lymphocytes. As noted, some tumours are infiltrated by lymphocytes. It is important to appreciate that lymphocytes are a highly heterogeneous cell population comprising of subgroups with different roles in the crosstalk of tumours and the host immune system. The most prominent cell type in anti-tumour immune responses are $CD8^+$ effector T cells, reflected in their prognostic significance and their use in adoptive T cell therapy. $T_H1$ polarised ($CD4^+$), as well as $CD4^+$ cytolytic T cells, have also been shown to induce strong anti-tumour responses. On the other hand, regulatory T cells and $T_H2$ polarised $CD4^+$ T cells have mostly been linked to pro-tumour effects. There is contradictory data on the role of $T_H7$ T cells and cancer in cancer immune responses.

Lymphocytes are the most radiosensitive cells of the hematopoietic system, as well as the entire body. This radiosensitivity is surprising for a non-dividing cell type, but may be related to robust apoptotic response pathways. The lethal dose required to reduce the surviving fraction of circulating lymphocytes by 90% (LD90) is only 3 Gy. 0.5 Gy already leads to significant cell death induction in lymphocytes. Such a dose could easily be reached in standard radiotherapy schedules.

Importantly, different lymphocyte subtypes show distinct radiosensitivity. Naïve $CD8^+$ effector T cells are more sensitive than memory T cells, while regulatory, T cells are relatively resistant. Furthermore, the state of T cells, the solid organs and the different location containing $CD8^+$ T cells also influences radiosensitivity. T cells that are proliferating are more radio-resistant than T cells in other state. With regard to the organs, the parenchymal CD8+ T cells in the solid lymphoid organs (lymph nodes and spleen) are found most radiosensitive, followed by those residing in liver and gut. The $CD8^+$ T cells located intratumorally have a higher radio-resistance, an increased motility and IFN-γ secretion compared to circulating $CD8^+$ T cells and T cells in unirradiated tumours. This may be due to changes in the tumour microenvironment wherein TGF-β is a key regulator in making the intratumoural T cells more radio-resistant. Similar differential effects have been observed concerning radiation dose rate with high dose rates leading to less lymphocyte death. These findings are well in line with clinical observations of decreased naïve T cells and enriched regulatory T cells in patients undergoing RT.

II. Analysis of the Clinical Literature

In many trials, the Common Terminology Criteria for Adverse Events (CTCAE) is used to differentiate between LP Grade 1 (<~1000-800/mm³), Grade 2 (<800-500/mm³), Grade 3 (<500-200 mm³), and Grade 4 (<200/mm³). Clinical factors that are associated with LP and key findings regarding LP for various cancers (glioblastoma (GBM), head and neck squamous cell carcinoma (HNSCC), nasopharyngeal cancer, non-small cell lung cancer (NSCLC), small cell lung cancer (SCLC), breast cancer, oesophageal cancer, pancreatic cancer, hepatocellular cancer (HCC), cervical cancer) are summarized below.

a. Factors that Influences LP

A disbalance in immuno-surveillance due to tumour suppressor systems can contribute to LP that is present before treatment. Also immunosuppressive medication or cancer related treatment can lead to pre- and post-treatment LP, e.g. corticosteroids, tyrosine-kinase inhibitors (TKIs), and immune checkpoint inhibitor. In addition, patients with immune related conditions, such as multiple comorbidities, autoimmune diseases, genetic disorders in innate or adaptive defense, or patients with a poor WHO performance state are known to have worse PFS and OS, probably related to a sub-optimally functioning immune system.

Also, treatment factors such as radiotherapy and chemotherapy have been shown to influence incidence and severity of LP.

Firstly, RT in general results in a lymphocyte reduction. More specifically, hypo-fractionation results in less reduction than normo- or hyper-fractionation. It has been found in a breast and a palliative cohort respectively, that LP was correlated with the number of fractions, independent of overall dose. Secondly, irradiating larger Gross Tumour Volumes (GTTV) in NSCLC patients has been associated with lower lymphocyte count but not with lower total leukocyte, neutrophil, or monocyte counts during RT. Thirdly, if lymphopoietic sites or organs containing large blood volumes are within the PTV, it will contribute to (longer duration of) LP. Several authors have also found that higher spleen irradiation doses (total dose of 50-60 Gy) were significantly correlated with more patients experiencing LP during RT for HCC or palliative RT. Based on these results, Liu et al recommend sparing of the spleen during abdominal irradiation. Furthermore a lower heart and lung dose resulted in less LP. Increasing the heart and long dose, severe loss of cardiopulmonary performance was seen in pre-clinical studies. Lastly, another important factor is the use of concurrent chemotherapy. Concurrent chemotherapy has been shown to have an impact on the severity of LP, whereas adjuvant chemotherapy may prolong the duration of LP. Importantly, different chemotherapy agents differ in LP impact.

b. Predictive/Prognostic Factors for OS after Radiation Induced LP

Many factors for OS and PFS have been investigated, including the role of LP. Ladbury et al. concluded that estimated dose of radiation to immune cells, Karnofsky performance status, not-otherwise-specified histology in NSCLC, lack of completion of chemotherapy, and smoking history are negative predictors for OS.

Disadvantageous prognostic factors for PIES and OS are baseline LP, early LP after chemotherapy treatment (5 or 15 days), LP after radiotherapy (RT) or LP after IO. Post-treatment LP has been negatively associated with poor tumour specific outcome in multiple cancer types e.g. GBM, HNSCC, cervical, oesophageal cancer, NSCLC, and pancreatic.

c. Effect of Combination Treatment. (RT+Chemo, RT+Chemo and/or IO)

As described previously, RT alone can induce or worsen LP. However, combining RT with systemic treatment has an even bigger impact on LP and treatment outcome, Cho et al, found that RT+checkpoint inhibitor treated NSCLC patients with LP pre-IO treatment had a significant poorer PFS (2.2 vs 5.9 months) and OS (5.7 vs 12.1 months) compared to patients who had normal lymphocyte counts before IO treatment. Furthermore they found that RT significantly increased the LP before start of IO, however irradiating with SABR, proton beam therapy, hypo-fractionation or radio-surgery reduced the risk on (increasing) RT-induced LP. The combination of RT with immunocytokines like IL2, IL7 or IL15 could eliminate LP due to their simulating effect to let the T cells develop, proliferate and survive.

Joseph et al found that after concurrent chemo-radiotherapy the absolute lymphocyte count (ALC) dropped significantly compared to ALC pre-treatment, but did not alter treatment outcome. In contrast, Grossman et al.

observed worse tumour control and shorter OS in GBM patients with depleted CD4+ T cell counts pre- and post-chemo-radiotherapy treatment. Furthermore, a prolonged duration of LP was also seen with RT. Similar results were found retrospectively by Wang et al, with almost 50% of SCLC patients experiencing severe LP and 70.4% prolonged lymphopenia of 3 months minimum after chemo-radiotherapy. For reasons not currently well understood, LP following RT can last from several months up to several years, whereas LP seen after sepsis or even chemotherapy alone tends to resolve more quickly.

It is reasonable to hypothesize that transient LP has a different effect on the outcome than persistent LP, Thus, the negative influence of RT on LP might be abolished by combinatorial approaches with IO, which could result in differences in the timing, the length and probably the grade of LP. This effect also depends on type of IO agent applied. On the other hand, it might indicate that the effect of adding IO to RT schedules lies primarily in a better functioning immune system, which in turn will be crucial to slow down the pace of microscopic disease spread in at least some patients.

d. Modelling Approaches to Predict the Incidence and Severity of LP

Taking into account the negative effect of LP on clinical outcomes, it is important to identify high risk patients timely and possibly adapt the treatment. Models predicting grade 4 RT-induced LP during chemo(radio)therapy for oesophageal cancer, or acute and late LP for prostate cancer have already been published, although the prostate model is yet to be validated. Also for NSCLC, a predictive risk model has been developed where clinical and genetic factors, e.g. lung V5>48%, age >65 years, >40 pack-years, and XRCC1 rs25487 AA genotype, are associated with severe RT-induced LP.

Several recent analyses have indicated that irradiation of cardio-vascular structures may lead not just to heart related morbidities but to unexplained reductions in OS following radiotherapy for NSCLC. A key question is whether this is mediated primarily through immune suppression. Contreras et al. showed that adjuvant chemotherapy and heart V50>25% are associated with lymphopenia at 4 months post RT. Thor et al, observed that out-of-treatment-field regional recurrence was statistically linked to lymphopenia at 2 months post RT. However, details of the relationship between patient/disease/treatment factors and lymphopenia, as well as the impact on disease progression remain elusive and need further study.

III. Recommendations for Clinical Trials

Figure 2:
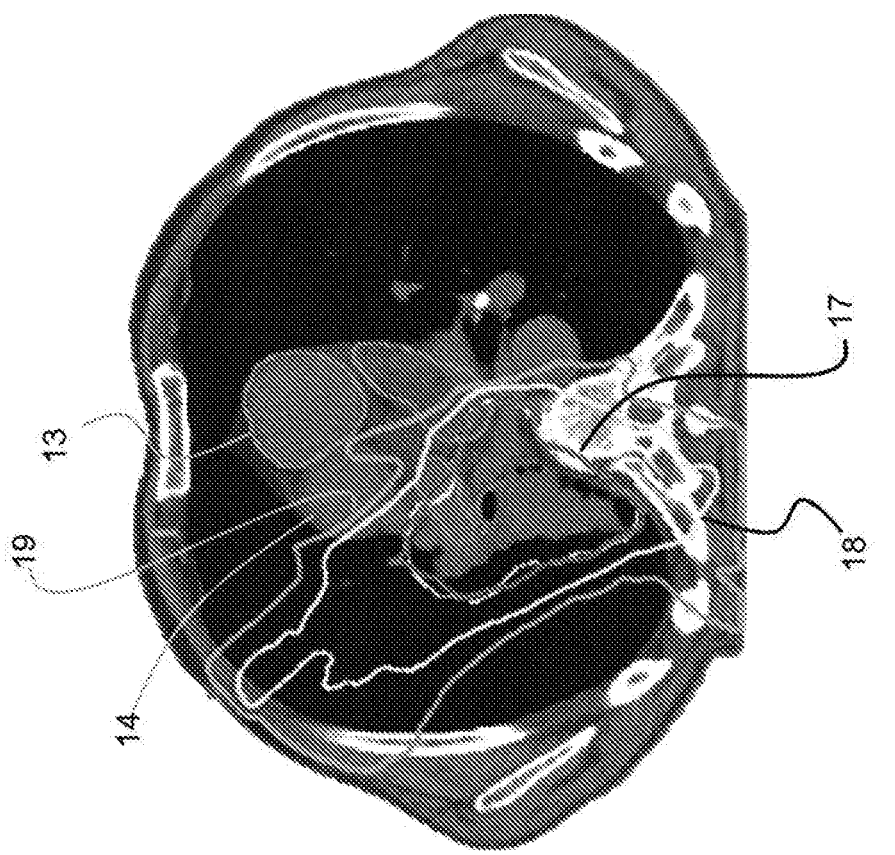
FIG. 2 in the left image shows a conventional dose distribution of a clinically applied radiation treatment plan, and in the right image shows an example of an optimized radiation plan applying the principles of the present invention.
Figure 2:
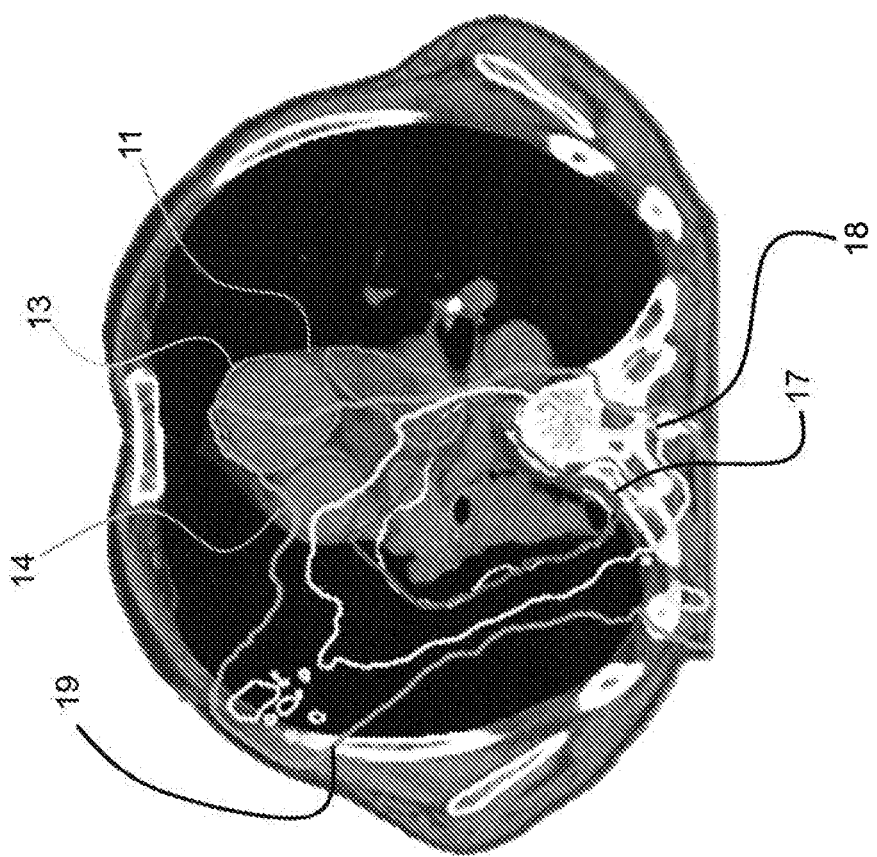
Figure 3:
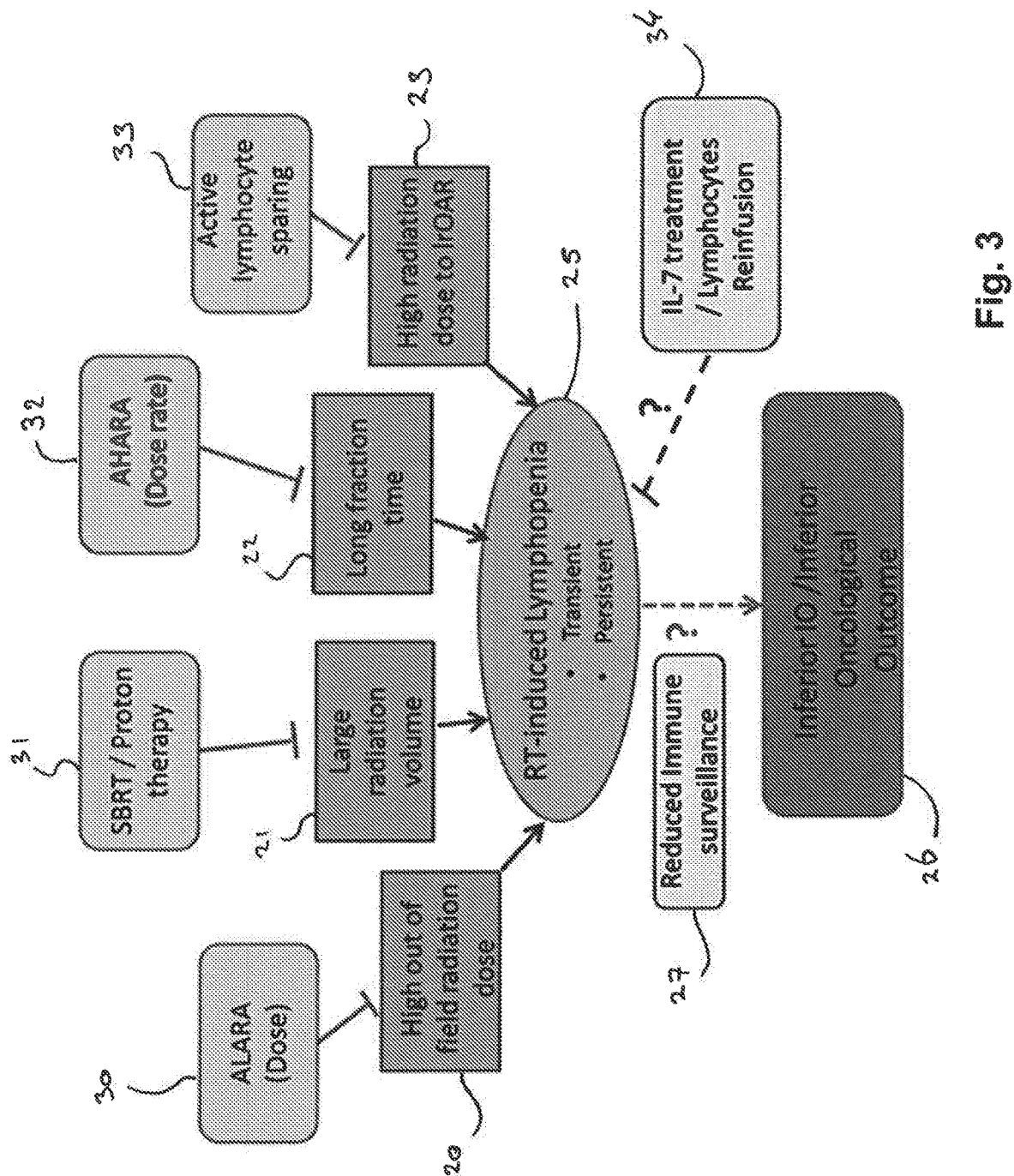
FIG. 3 shows a model linking radiation to lymphopenia and to inferior oncological outcomes, and steps to overcome this.

There is a large body of literature evidence showing that incidence and severity of LP are associated with patient and treatment characteristics, but also showing the importance for clinical outcomes. Moreover, we have identified 437 trials listed in clinicaltrial.gov combining IO with RT, September 2019, indicating that combining RT with IO is increasingly adopted as treatment strategy. To improve clinical outcomes, but also to gain the most of RT-IO combination treatment, it is of utmost importance to establish recommendations for RT planning with regard to lymphocyte dose. However, as indicating absolute dose constraints is not (yet) possible, we propose to apply the As Low As Reasonably Achievable (ALARA) principle to Lymphocyte-related Organs At Risk (LOARs) without compromising irradiation of the PTV (see FIGS. 1 and 2) and keeping the constraints for "conventional" organs at risk such as lung, heart and spinal cord, as recommended in clinical protocols (FIG. 3). Optionally, in a preferred embodiment, it is also proposed to apply the As High As Reasonably Achievable (AHARA) principle for the dose rate and beam-on-time to spare the circulating blood cells, FIG. 1 provides an example of segmentation for lung cancer treatment. The left image illustrates the delineation of the Lymphocyte-related Organs At Risk (LOAR, i.e. OAR's that are also LRO's), i.e. the heart 11, and the lymphocyte-rich-organs (LRO's) the arteries 13 and the veins 14. The right image shows the delineation of the LRO's 11, 13 and 14 and the planned target volume 15 where a tumor is located. FIG. 2 shows a standard dose distribution of a clinically applied radiation treatment plan in the left image, and an example of an optimized radiation plan applying the (As Low As Reasonably Achievable) ALARA principle in the right image. The figure shows the heart 11, the arteries 13 and the veins 14, properly delineated for segmentation. Furthermore, the figure shows the applied dose distribution by contour lines 17, 18 and 19. Contour line 17 shows the area where the applied dose is greater than or equal to 60 Gray, contour line 18 shows the area where the applied dose is greater than or equal to 40 Gray, and contour line 19 shows the area where the applied dose is greater than or equal to 20 Gray. The left figure, wherein a standard conventional close regime has been applied, clearly illustrates that a relatively large fraction of the LRO's (the heart 11, the arteries 13 and the veins 14) still receives a dose of over 20 Gray of radiation. The right figure, showing the distribution obtained using a treatment planning method in accordance with an embodiment, shows that the fraction of the LRO's that receives a dose level of over 20 Gray is strongly reduced as compared to the left image. This demonstrates that sparing of LOAR is feasible without compromising dose coverage of the target volume or increasing dose to OARs important in clinical radiotherapy planning.

FIG. 3 shows a model linking radiation to lymphopenia and to inferior oncological outcomes. In this figure, the factors 20, 21, 22 and 23 are all suspected to contribute to radiation treatment induced lymphopenia 25. These factors include a high out of field radiation dose 20, a large radiation volume 21, a long fraction time 22 and a high radiation dose to the LRO's 23, This, in turn, is suspected to contribute to inferior oncological outcome 26. Furthermore, a disbalance in immuno-surveillance 27 due to tumour suppressor systems (e.g. due to therapeutic application of cytostatics) may likewise reduce the effect of the radiation treatment. To overcome, the following measures are proposed. A high out of field radiation dose 20 may be mitigated by applying the ALARA principle 30 as suggested herewith. A large radiation volume 21 may be mitigated by applying stereotactic body radiotherapy (SBRT) and/or proton therapy as suggested in 31. A long fraction time 22 may be reduced by applying the as high as reasonably achievable (AHARA) principle 32 on the dose rate applied. Furthermore, the a high radiation dose to the LRO's 23 may be mitigated by applying active lymphocyte sparing 33. If the effects are insufficient, lymphocyte (re)infusion or a treatment with a lymphocyte growth factor such as an IL-7 treatment in accordance with step 34 may be applied to improve.

Furthermore, systematic recording of dose-volume and dose-rate statistics for those LOARs, as well as longitudinal lymphocyte counts is recommended. These data, routinely available at most treatment centres, would allow the design of strategies to predict and to some extent prevent RT-induced LP. It would also help to answer the main remaining hypothesis whether maintaining and/or restoring optimal lymphocyte counts may improve treatment. RT outcomes, or increase the efficacy of IO.

These data can only be obtained if relevant organs are systematically delineated. These include the large vessels, heart, and any irradiated lymphoid organs such as bone marrow (e.g. pelvic bones, vertebrae, large long bones), nodal regions not included in the CTV, spleen, and thymus in children. To facilitate the segmentation of large vessels, we propose to explore the use of contrast-enhanced computed tomography (CT), acquiring data during the early blood dominated phases. Automatic segmentation methods based on deep learning will certainly facilitate this process. Dose, fractionation, dose rate, and mean doses to LOARs should be reported as a minimum. Blood can be seen as a "moving OAR", therefore long irradiation times should be avoided, Instead, high dose rate irradiation, following the principle of "As High As Reasonably Achievable" (AHARA) should be favoured, e.g. using flattening filter-free irradiation.

IV. Prospects

As it is clear that the role of the immune system is very important for clinical outcomes, much research currently focuses on unravelling the complex interplay between treatment characteristics and the immune system and how to influence this relationship. In an attempt to preserve the immune system from the effects of radiation and chemotherapy, lymphocytes were isolated before treatment, stored and administered again to the patient upon treatment completion (NCT01653834).

New imaging methods may also become important. New sequences of Magnetic Resonance (MR) enable to quantify blood volume in vessels and organs using non-contrast MR imaging such as the venography technique or velocity-selective (VS) pulse trains. These new approaches will allow us not only to quantify blood volume without contrast in the vascular system but also in organs such as liver, brain and spleen. New positron emission tomography (PET) tracers that can precisely track $CD8^+$ T cells are also under development. Furthermore, the combination of new strategies and precise technological developments, such as a Magnetic Resonance Linear Accelerator (MR-linac), will make it possible to not only more precisely identify and track LOARs, but also avoid or restrict radiation dose to these LOARs. To facilitate comparable analyses, new autosegmentation/AI methods could be distributed using portable container technology to extract dosimetric characteristics of the LOARs.

V. Conclusion

The breakthrough improvement in outcomes by IO alone, or in combination with RT, has renewed the interest of the scientific community on strategies to predict and avoid RT-associated LP that may be immunosuppressive. There is a convergence of preclinical and clinical evidence correlating unintentional irradiation of LOARs with LP and poor outcomes. Preclinical studies definitively show an established causal relationship between lymphocyte depletion and the effectiveness of IO. Therefore, we propose that the ALARA principle should be applied to LOARs, and dose-rates should be kept as high as practical to spare peripheral blood lymphocytes, in particular in the context of clinical trials combining RT with IO. Furthermore, we urge investigators of clinical RT trials with an immune component to systematically record the potentially-relevant dosimetric and hematopoietic parameters. Such unique data will hopefully lead to predictive models that will allow us to predict and prevent RT-induced LP in an individualised approach for each patient in order to answer the key unresolved question: whether maintaining and/or restoring optimal lymphocyte counts independently improves RT or IO outcomes.

VI. Overview of Workflow

Figure 4:
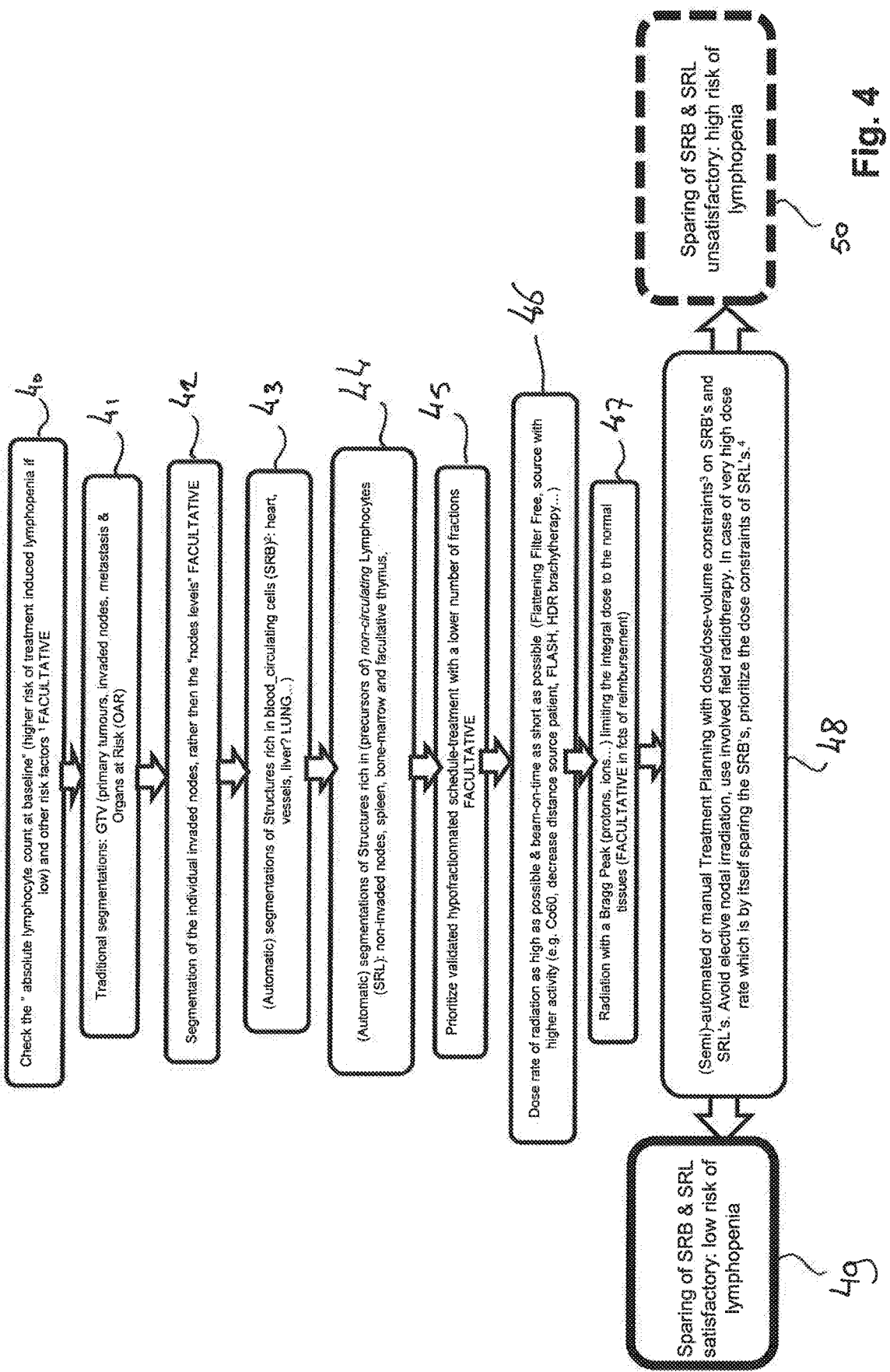
FIG. 4 shows method steps in accordance with an embodiment.

FIG. 4 shows a workflow overview of a method in accordance with an embodiment of the present invention. In accordance with embodiments, the first optional step 40 will be to check the "absolute lymphocyte count at baseline" and other risk factors. If the absolute lymphocyte count is low, there already is a higher risk of treatment induced lymphopenia if low. The other risk factors for example include (but are not limited to): smoking, a large tumour volume, past/present chemotherapy, and certain gene polymorphism (e.g. XRCC1 rs25487 AA genotype).

In step 41, the traditional segmentations are performed, such as GTV (primary tumours, invaded nodes, metastasis) and organs-at-risk (OAR's) In respect of the invaded nodes, optionally, step 42 may be carried out to perform segmentation of the individual invaded nodes, rather than the "nodes levels".

Next in step 43, in accordance with the invention, segmentation of structures rich in blood circulating cells (SRB) is performed. These include the structures taking a part in blood circulation, such as the heart, vessels, the lungs, the brain and optionally the liver. As may be appreciated, any parts of these LRO's and LOAR's that are affected by neoplasm (i.e. tumour) growth may be part of the target volume, and cannot be spared and therefore may be excluded. It may be appreciated that, for these areas, it is still possible to make choices to e.g. apply the required dose with an AHARA dose rate to reduce the irradiation time and thereby the number of irradiated lymphocytes. Furthermore, the segmentation of step 43 may (advantageously) be performed automatically using e.g. a machine learning data processing model that has been trained to perform automatic contour recognition on medical image data for recognizing a contour of an organ or a neoplasm. Such an artificial intelligence model for example has been described in Dutch patent application number NL 2024889 relating to an image data processing method, a method of training a machine learning data processing model and image processing system, in particular the delineation, segmentation and contour recognition steps (e.g. see FIGS. 4, 5, 7-13, 15 and 16).

In step 44, in accordance with the invention, segmentation of structures rich in non-circulating lymphocytes (SRL) or precursors thereof is performed. These may for example include the non-invaded lymph nodes, spleen, bone-marrow and optionally the thymus. Again, this step 44 may (advantageously) be performed automatically using e.g. a machine learning data processing model that has been trained to perform automatic contour recognition on medical image data for recognizing a contour of an organ or a neoplasm. Such an artificial intelligence model for example has been described in Dutch patent application number NL 2024889 relating to an image data processing method, a method of training a machine learning data processing model and image processing system, in particular the delineation, segmentation and contour recognition steps (e.g. see FIGS. 4, 5, 7-13, 15 and 16).

Optionally, in step 45, clinically validated isoeffective-isotoxic hypo-fractionated schedule-treatment with a lower number of fractions may be prioritized, e.g. to further reduce the risk on (increasing) RT-induced LP.

In step 46, the dose regimes are set. The leading first dose regime will be determined based on the need to target the tumor effectively. The second dose regime will add requirements to be taken along during treatment planning, and typically may require the (dose to the OAR's to be as low as possible (ALARA). The third dose regime considers the LRO's and LOAR's and typically will set, as constraint, the dose delivered to the LOAR's in accordance with the ALARA principle while optionally setting the dose rate in accordance with the AHARA principle. For example, the dose rate of radiation may be set to be as high as possible and the beam-on-time as short as possible. A flattening filter free approach may be set, a radiation source with higher activity (e.g. Cobalt 60) may be prescribed, a decrease of distance between the radiation source and the patient may be proposed to meet the dose requirements, a FLASH radiation approach may be proposed, and/or HDR brachytherapy may be prescribed. Furthermore, in accordance with optional step 47, radiation with a Bragg peak (protons, ions . . . ) may be prescribed. This limits the integral dose to normal tissues.

Step 48 eventually performs the treatment planning with dose/dose-volume constraints on SRB's and SRL's (i.e. the LRO's). The dose/dose-volume constraints may include, for example, a mean dose (MD) per structure (SRB)<8% of the prescribed dose in the first dose regime (e.g. <5 Gy to the heart for a prescribed dose of 60 Gy in 30 fractions). An example of dose volume constraints for the pelvic bone marrow (BM), it would be a low volume receiving ≥40 Cy (V40<100 cc) or for lung a V5<50%. The treatment planning may be set up to avoid elective nodal irradiation, and to use involved field radiotherapy. In case of a very high dose rate which is by itself sparing the SRB's, the dose constraints of SRL's are to be prioritized. The same dose constraints should be used for the GTV, CTV and OAR, however optionally the constraints to the SRB and SRL should be prioritized over the high-dose conformity of the GTV, Optionally when the radiation will be followed by an immunotherapy the third radiation dose regime is prioritized over the first radiation dose regime in term of prescribed dose, high dose conformity, margins reduction, volume reduction of PTV, CTV, GTV, subvolume irradiation. In other words when the effect of the systemic treatment with immunotherapy need to be prioritized over the local treatment e.g. because the patient has metastasis or is likely to have micrometastases that will not be irradiated, the lymphocytes need to be spared at any cost even if it is at the cost of the completeness of the irradiation of target volume, for example it can be decided for example to suppress the PTV or even irradiate only part of the GTV.

The outcome may then be either that, in accordance with 49, the sparing of SRB and SRL (LOAR's) is satisfactory, hence providing a low risk of lymphopenia. However, if in accordance with 50, it is determined that the sparing of SRB and SRL in accordance with the treatment plan is unsatisfactory, and hence a high risk of lymphopenia would remain, additional measures as illustrated and described below with reference to FIG. 5 may be considered.

Figure 5:
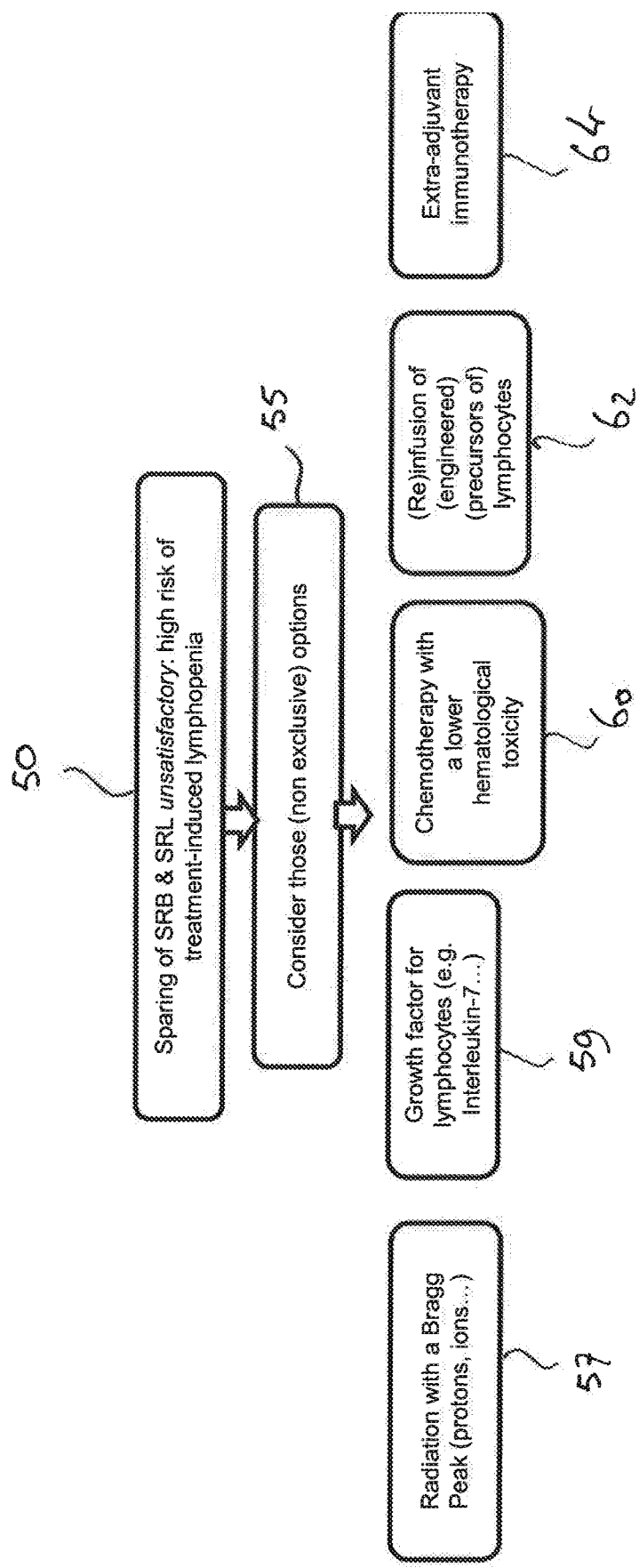
FIG. 5 shows additional method steps in accordance with an embodiment.

FIG. 5 starts with step 50 described above, wherein it has been determined that the sparing of SRB and SRL in accordance with the treatment plan is unsatisfactory. Step 55 then proposes to consider a number of optional (and non-exclusive) possibilities. In accordance with step 57, if not already performed in step 47, radiation with a Bragg peak (protons, ions . . . ) may be considered. Furthermore, as suggested in 59, treatment of the patient with a growth factor for lymphocytes (e.g. Interleukin-7) may be considered. As a further option, it may be considered to treat the patient by chemotherapy with a lower hematological toxicity (step 60). Another option will be to perform infusion or reinfusion of a subclass of lymphocytes and/or engineered and/or expanded) (precursors of) autologous or allogenic or synthetic) lymphocytes (step 62). Another option in accordance with 64 will be to treat the patient with extra-adjuvant immunotherapy.

Figure 6:
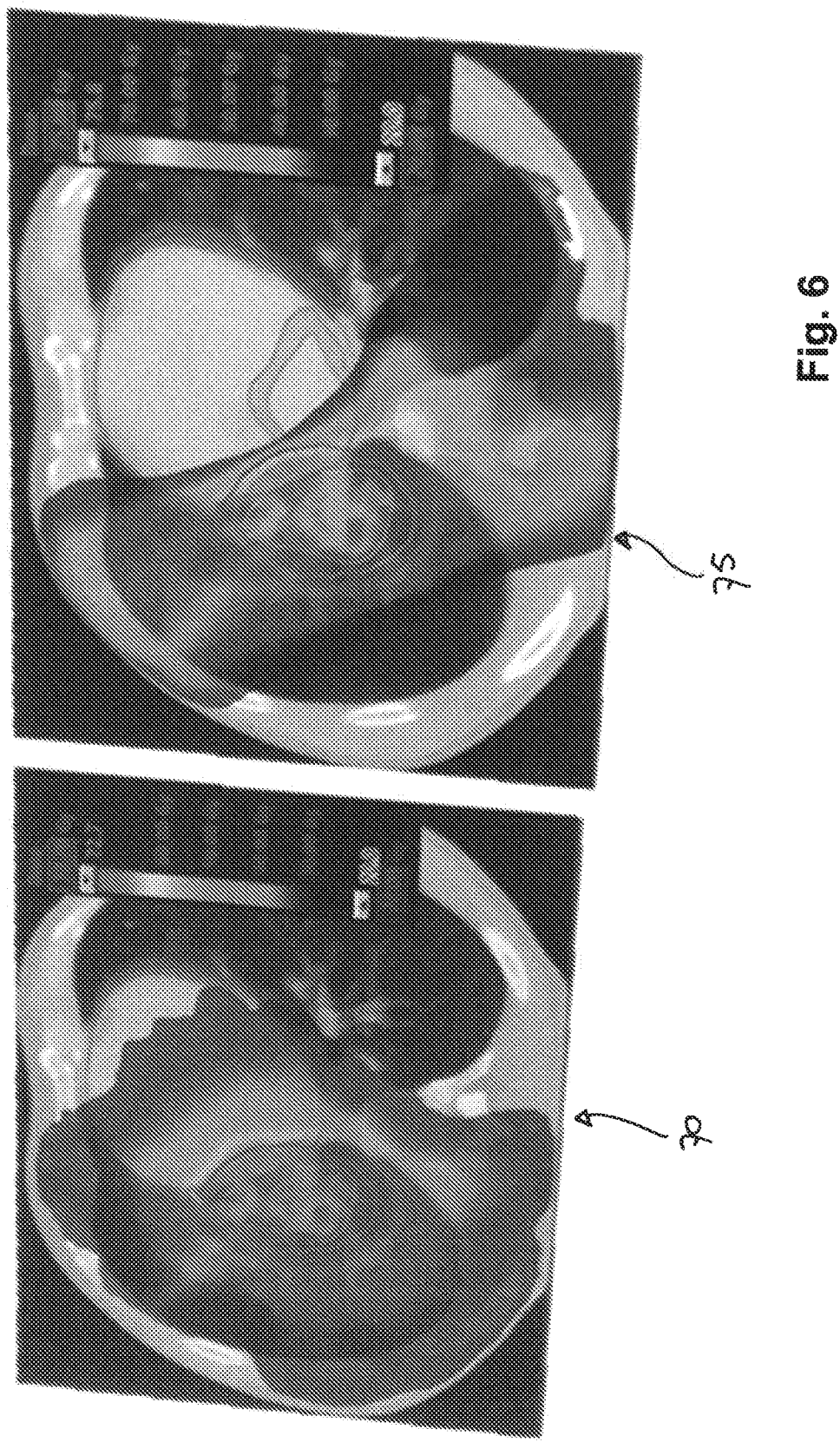
FIG. 6 shows images of applied radiation in accordance with an optimized treatment plan obtained in accordance with an embodiment of the invention.

FIG. 6 further shows an example of a radiation distribution in accordance with original treatment plan 70, which is modified using a method in accordance with the present invention into a modified treatment plan to spare lymphocytes, yielding the radiation distribution depicted in 75. Clearly, the amount of radiation received by the heart is far less in picture 75, without the radiation in the target volume to be mitigated by the modified treatment plan.

Figure 7:
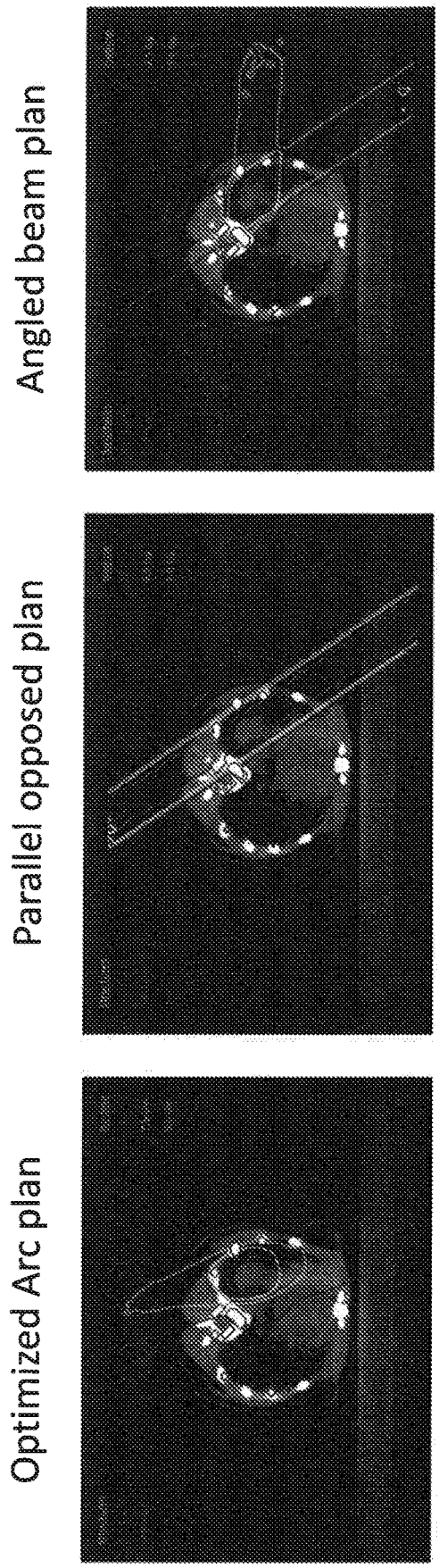
FIG. 7 from let to right, shows a murine tumour (Non Small Cell Lung Cancer) irradiated with an optimized are and a rather high heart dose (1.4 GY) while the simple plans (parallel opposed plan and angled beam plan give the same dose to the tumour but a lower dose to the heart.

FIG. 7 from let to right, shows a murine tumour (Non Small Cell Lung Cancer) irradiated with an optimized are and a rather high heart dose (1.4 Gy) while the simple plans (parallel opposed plan and angled beam plan give the same dose to the tumour but a lower dose to the heart.

The present invention has been described in terms of some specific embodiments thereof. It will be appreciated that the embodiments shown in the drawings and described herein are intended for illustrated purposes only and are not by any manner or means intended to be restrictive on the invention. It is believed that the operation and construction of the present invention will be apparent from the foregoing description and drawings appended thereto. It will be clear to the skilled person that the invention is not limited to any embodiment herein described and that modifications are possible which should be considered within the scope of the appended claims. Also kinematic inversions are considered inherently disclosed and to be within the scope of the invention. Moreover, any of the components and elements of the various embodiments disclosed may be combined or may be incorporated in other embodiments where considered necessary, desired or preferred, without departing from the scope of the invention as defined in the claims.

In the claims, any reference signs shall not be construed as limiting the claim. The term 'comprising' and 'including' when used in this description or the appended claims should not be construed in an exclusive or exhaustive sense but rather in an inclusive sense. Thus the expression 'comprising' as used herein does not exclude the presence of other elements or steps in addition to those listed in any claim. Furthermore, the words 'a' and 'an' shall not be construed as limited to 'only one', but instead are used to mean 'at least one', and do not exclude a plurality. Features that are not specifically or explicitly described or claimed may be additionally included in the structure of the invention within its scope. Expressions such as: "means for . . . " should be read as: "component configured for . . . " or "member constructed to . . . " and should be construed to include equivalents for the structures disclosed. The use of expressions like: "critical", "preferred", "especially preferred" etc. is not intended to limit the invention. Additions, deletions, and modifications within the purview of the skilled person may generally be made without departing from the spirit and scope of the invention, as is determined by the claims. The invention may be practiced otherwise then as specifically described herein, and is only limited by the appended claims.

The invention claimed is:

1. A method of providing a radiation treatment plan for treatment of a neoplasm in a human or animal body using a planning system, the method including the steps of:

obtaining, by the planning system using at least one imaging system, an image of at least a part of the body including the neoplasm;

obtaining, by the planning system, first segmentation data for segmenting, in the image, at least one target volume to be targeted with radiation;

identifying, by the planning system, one or more organs-at-risk in the image, and obtaining second segmentation data for segmenting the or each organs-at-risk;

wherein the method further comprises:

identifying, by the planning system and in addition to the identified organs-at-risk, one or more lymphocyte-rich-organs in the image, and obtaining third segmentation data for segmenting the or each lymphocyte-rich-organ;

obtaining, by the planning system, radiation dose regime data, wherein the radiation dose regime data includes a first dose regime data for the target volume, second dose regime data for the or each organ-at-risk, and third dose regime data for the or each lymphocyte-rich-organ, wherein the second dose regime data is different form the first dose regime data and wherein the third dose regime data is different from the second dose regime data and different from the first dose regime data;

determining, by the planning system, a radiation treatment plan, wherein the radiation treatment plan provides treatment process parameters for operating one or more radiation beams for radiation treatment of the neoplasm, wherein the process parameters provided by the radiation treatment plan are determined such as to:

apply the radiation at a first radiation dose to the target volume which corresponds with the first dose regime data;

apply the radiation at a minimized second radiation dose to the or each organs-at-risk which corresponds with the second dose regime data; and apply the radiation at a third radiation dose to the or each lymphocyte-rich-organ which corresponds with the third dose regime data, wherein the third radiation dose amount is minimized.

2. The method according to claim 1, wherein the process parameters include one or more of a group comprising: a dose indication, such as an absolute dose, a relative dose, a dose per volume, or a dose per weight; a dose rate indication, such as an absolute dose rate, a dose rate per volume, or a dose rate per weight; a number of radiation sources to be applied; a type of radiation source to be applied; a distance between a radiation source and a target volume or a patient; indications of a filter to be used with one or more radiation sources; an indication of radiation intensity to be applied over time, such as a FLASH radiation profile; irradiation time duration; an indication on whether or not to apply a flattening filter; an indication on beam focusing; an indication on an intended location of a Bragg peak; an indication on further treatment steps, such as a necessity of a blood or lymphocyte transfusion or treatment with a lymphocyte growth factor after irradiation.

3. The method according to claim 1, wherein for enabling to apply a third radiation dose to the or each lymphocyte-rich-organ which corresponds with the third dose regime data, the step of determining a radiation treatment plan further includes determining the process parameters such as to apply the third radiation dose with a maximized dose rate or minimized beam-on-time for decreasing an irradiation time duration.

4. The method according to claim 3, wherein for maximizing the dose rate the process parameters are determined such as to include at least one of:

an indication of a type of radiation source to be applied, wherein the indicated type of radiation source is determined for maximizing a radiation source activity, such as a Cobalt 60 radiation source;

an indication of a distance between a radiation source and a target volume or a patient such as to achieve the maximized dose rate;

an indication to apply a radiation source in absence of a flattening filter;

an indication to optimize beam energy to decrease beam-on-time;

an indication to perform a FLASH irradiation, wherein the FLASH irradiation includes irradiating with a dose rate of at least 40 Gray per second, preferably at least 50 Gray per second, for a duration of at most 500 milliseconds, preferably at most 200 milliseconds, using a radiation type selected from a group comprising: electrons, protons, photons, ions such as carbon ions, photons, or particles.

5. The method according to claim 1, wherein for enabling to apply a third radiation dose to the or each lymphocyte-rich-organ which corresponds with the third dose regime data, the step of determining a radiation treatment plan further includes determining the process parameters such as to include an indication of a radiation type providing a sufficient Bragg peak such as proton radiation or carbon ions, and an indication of an intended location of the Bragg peak such as to focus the Bragg peak in the target volume.

6. The method according to claim 1, wherein for enabling to apply a third radiation dose to the or each lymphocyte-rich-organ which corresponds with the third dose regime data, the step of determining a radiation treatment plan further includes determining the process parameters such as to at least one of:

apply the radiation at the first radiation dose at the target volume with a minimal number of radiation beams;

apply the radiation at the first radiation dose at the target volume using a maximized number of non-moving beams, preferably using only static beams;

to avoid elective nodal irradiation; or to segment the involved lymph nodes based on imaging or biopsy or fine needle aspiration and irradiate those involve nodes as target volume rather than to irradiate the totality of the nodes levels.

7. The method according to claim 1, wherein the neoplasm is irradiated during a number of fractions over a period of time, and wherein at least one of:

the process parameters provided by the radiation treatment plan are determined such as to apply an adaptive radiation treatment plan, and wherein the process parameters are adapted for each fraction for minimizing the third radiation dose during the respective fraction; or the radiation treatment is hypo-fractionated by decreasing the number of fractions and increasing the dose per fraction.

8. The method according to claim 1, wherein the image is a three dimensional image.

9. The method according to claim 1, wherein the at least one imaging system configured for applying at least one image modality.

10. The method according to claim 1, wherein the third dose regime data indicates that the applied third radiation dose is at most 33% of a prescribed dose in the first radiation dose regime, preferably at most 18% of a prescribed dose in the first radiation dose regime, more preferably at most 8% of a prescribed dose in the first radiation dose regime.

11. The method according to claim 1, wherein the lymphocyte-rich-organs include one or more of a group comprising: a heart; a large blood vessel, such as a thoracic aorta, an abdominal aorta, the superior or inferior vena cava, a carotid or any large artery (the iliac, mesenteric, subclavian, femoral arteries . . . ); a heart ventricle or atrium, such as any one or more of the left and right ventricle and the left and right atrium; a spleen; a bone; a bone marrow; a brain; a lung, a liver.

12. The method according to claim 1, wherein one or more of the steps of:
    obtaining the first segmentation data of the target volume,
    obtaining the second segmentation data of the or each organs-at-risk, and
    obtaining the third segmentation data of the or each lymphocyte-rich-organ,
    is performed using a machine learning data processing model that has been trained to perform automatic contour recognition on medical image data for recognizing a contour of an organ or a neoplasm.

13. The method according to claim 1, wherein the step of identifying one or more lymphocyte-rich-organs comprises differentiating lymphocyte-rich-organs with mainly circulating cells and lymphocyte-rich-organs with mainly non-circulating cells and applying a further different dose regime to each.

14. The method according to claim 1, wherein the third radiation dose regime is prioritized over the first radiation dose regime.

15. A radiation treatment planning system configured for determining a treatment plan for treatment of a neoplasm in a human or animal body, the system including or being communicatively connectable to a data storage element for storing data, and comprising a controller, wherein the controller is configured for receiving instructions and for enabling the system to perform the steps of:
    obtaining, by the planning system using at least one imaging system, an image of at least a part of the body including the neoplasm;
    obtaining, by the planning system, first segmentation data for segmenting, in the image, at least one target volume to be targeted with radiation;
    identifying, by the planning system, one or more organs-at-risk in the image, and obtaining second segmentation data for segmenting the or each organs-at-risk;
wherein the method further comprises:
    identifying, by the planning system and in addition to the identified organs-at-risk, one or more lymphocyte-rich-organs in the image, and obtaining third segmentation data for segmenting the or each lymphocyte-rich-organ;
    obtaining, by the planning system, radiation dose regime data, wherein the radiation dose regime data includes a first dose regime data for the target volume, second dose regime data for the or each organ-at-risk, and third dose regime data for the or each lymphocyte-rich-organ, wherein the second dose regime data is different form the first dose regime data and wherein the third dose regime data is different from the second dose regime data and different from the first dose regime data;
    determining, by the planning system, a radiation treatment plan, wherein the radiation treatment plan provides treatment process parameters for operating one or more radiation beams for radiation treatment of the neoplasm, wherein the process parameters provided by the radiation treatment plan are determined such as to:
        apply the radiation at a first radiation dose to the target volume which corresponds with the first dose regime data;
        apply the radiation at a minimized second radiation dose to the or each organs-at-risk which corresponds with the second dose regime data; and
        apply the radiation at a third radiation dose to the or each lymphocyte-rich-organ which corresponds with the third dose regime data, wherein the third radiation dose amount is minimized.

16. The system according to claim 15, wherein the controller is configured for determining the process parameters to include one or more of a group comprising: a dose indication, such as an absolute dose, a dose per volume, or a dose per weight; a dose rate indication, such as an absolute dose rate, a dose rate per volume, or a dose rate per weight; a number of radiation sources to be applied; a type of radiation source to be applied; a distance between a radiation source and a target volume or a patient; indications of a filter to be used with one or more radiation sources; an indication of radiation intensity to be applied over time, such as a FLASH radiation profile; irradiation time duration; an indication on whether or not to apply a flattening filter; an indication on beam focusing; an indication on an intended location of a Bragg peak; an indication on further treatment steps, such as a necessity of a blood transfusion or treatment with a lymphocyte growth factor after irradiation.

17. The system according to claim 15, wherein the system comprises or is communicatively connectable to the at least one imaging system.

18. The system according to claim 15, wherein the system comprises or is communicatively connectable to a machine learning data processing model that has been trained to perform automatic contour recognition on medical image data for recognizing a contour of an organ or a neoplasm, wherein the machine learning data processing model is configured for performing one or more of the steps of:
    obtaining the first segmentation data of the target volume,
    obtaining the second segmentation data of the or each organs-at-risk, and
    obtaining the third segmentation data of the or each lymphocyte-rich-organ.

19. A method of treating a patient with radiation treatment, where the patient is suffering from neoplasm growth, wherein the radiation treatment is performed in accordance with a radiation treatment plan for treatment of a neoplasm in the patient's body, the method including the steps of:
    obtaining, using at least one imaging system, an image of at least a part of the body, wherein the part of the body includes the neoplasm;
    segmenting in the image at least one target volume to be targeted with radiation;
    identifying one or more organs-at-risk in the image and segmenting the or each organ-at-risk;
wherein the method further comprises:
    identifying, in addition to the identified organs-at-risk, one or more lymphocyte-rich-organs in the image, and segmenting the or each lymphocyte-rich-organ;
    determining a radiation dose regime, wherein the radiation dose regime includes a first dose regime for the target volume, a second dose regime for the or each organ-at-risk, and a third dose regime for the or each lymphocyte-rich-organ, and wherein the first dose regime, the second dose regime and the third dose regime are different from each other;

determining the radiation treatment plan by determining treatment process parameters for operating one or more radiation beams for said radiation treatment of the neoplasm, wherein the process parameters are determined such as to:

apply the radiation at a first radiation dose to the target volume which corresponds with the first dose regime;

apply the radiation at a minimized second radiation dose, which corresponds with the second dose regime, to the or each organ-at-risk; and apply the radiation at a third radiation dose, which corresponds with the third dose regime, to the or each lymphocyte-rich-organ, wherein the third radiation dose amount is minimized.

20. The method according to claim 19, wherein the process parameters include one or more of a group comprising: a dose indication, such as an absolute dose, a dose per volume, or a dose per weight; a dose rate indication, such as an absolute dose rate, a dose rate per volume, or a dose rate per weight; a number of radiation sources to be applied; a type of radiation source to be applied; a distance between a radiation source and a target volume or a patient; indications of a filter to be used with one or more radiation sources; an indication of radiation intensity to be applied over time, such as a FLASH radiation profile; irradiation time duration; an indication on whether or not to apply a flattening filter; an indication on beam focusing; an indication on an intended location of a Bragg peak; an indication on further treatment steps, such as a necessity of a blood transfusion or treatment with a lymphocyte growth factor after irradiation.

21. The method according to claim 19, wherein the step of determining a treatment plan includes a step of:

determining a preliminary treatment plan and calculating a third radiation dose that will be received by the or each lymphocyte-rich-organ what radiation treatment is performed in accordance with the preliminary radiation treatment plan;

comparing the calculated third radiation dose with a dose threshold for the or each lymphocyte-rich-organ, and in case the calculated third radiation dose exceeds the dose threshold, perform one or more modified treatment steps in accordance with a modified treatment plan different from the preliminary treatment plan.

22. The method according to claim 21, wherein the one or more modified treatment steps include applying the third radiation dose with a maximized dose rate for decreasing an irradiation time duration.

23. The method according to claim 22, wherein for applying the third radiation dose with the maximized dose rate, the method includes one or more of the following steps:

applying the radiation using a type of radiation source with a radiation source activity of at least 20 terabecquerel per gram (TBq/g), such as a Cobalt 60 radiation source;

applying the radiation at a distance between a radiation source and a target volume or a patient determined such as to achieve the maximized dose rate;

applying the radiation using a radiation source in absence of a flattening filter;

applying the radiation by performing a FLASH irradiation method, wherein the FLASH irradiation method includes irradiating with a dose rate of at least 40 Gray per second, preferably at least 50 Gray per second, for a duration of at most 500 milliseconds, preferably at most 200 milliseconds, using a radiation type selected from a group comprising: electrons, protons, photons, ions such as carbon ions, photons, or particles.

24. The method according to claim 21, wherein the one or more modified treatment steps include: applying the radiation using a radiation type providing a Bragg peak, such as proton radiation, and modifying the radiation beam such as to focus the Bragg peak in the target volume.

25. The method according to claim 21, wherein the one or more modified treatment steps include:

applying the radiation using at the first radiation dose at the target volume with a minimal number of radiation beams;

applying the radiation at the first radiation dose at the target volume using a maximized number of non-moving beams, preferably using only static beams;

to avoid elective nodal irradiation; or to segment the involved lymph nodes based on imaging or biopsy or fine needle aspiration and irradiate those involve nodes as target volume rather then to irradiate whole nodes levels.

26. The method according to claim 19, wherein the method includes applying an adaptive radiation treatment plan, wherein the neoplasm is irradiated during a number of passes over a period of time, and wherein the process parameters are adapted for each pass for minimizing the third radiation dose during the respective pass.

27. The method according to claim 19, wherein the image is a three dimensional image.

28. The method according to claim 19, wherein the at least one imaging system configured for applying at least one image modality.

29. The method according to claim 19, wherein the third dose regime data indicates that the applied third radiation dose is at most 33% of a prescribed dose in the first radiation dose regime, preferably at most 18% of a prescribed dose in the first radiation dose regime, more preferably at most 8% of a prescribed dose in the first radiation dose regime.

30. The method according to claim 19, wherein the lymphocyte-rich-organs include one or more of a group comprising: a heart; a large blood vessel, such as a thoracic aorta, an abdominal aorta, the superior or inferior vena cava, a carotid or any large artery (the iliac, mesenteric, subclavian, femoral arteries . . . ); a heart ventricle or atrium, such as any one or more of the left and right ventricle and the left and right atrium; a spleen; a bone; a bone marrow; a brain; a lung, the thymus.

31. The method according to claim 19, wherein one or more of the steps of:

segmenting of the target volume, segmenting of the or each organs-at-risk, and segmenting of the or each lymphocyte-rich-organ, is performed using a machine learning data processing model that has been trained to perform automatic contour recognition on medical image data for recognizing a contour of an organ or a neoplasm.

32. The method according to claim 19, wherein the neoplasm is irradiated during a number of fractions over a period of time and wherein the radiation treatment is hypofractionated by decreasing the number of fractions and increasing the dose per fraction.

33. The method according to claim 19, wherein the step of identifying one or more lymphocyte-rich-organs comprises differentiating lymphocyte-rich-organs with mainly circulating cells and lymphocyte-rich-organs with mainly non-circulating cells and applying a further different dose regime to each.

34. The method according to claim 19, wherein the third radiation dose regime is prioritized over the first radiation dose regime.

\* \* \* \* \*